(12) United States Patent
Jalbert

(10) Patent No.: US 11,007,293 B1
(45) Date of Patent: May 18, 2021

(54) TOUCHLESS SANITIZING ELEVATOR BUTTON

(71) Applicant: Vincent Paul Jalbert, East Lyme, CT (US)

(72) Inventor: Vincent Paul Jalbert, East Lyme, CT (US)

( * ) Notice: Subject to any disclaimer, the term of this patent is extended or adjusted under 35 U.S.C. 154(b) by 0 days.

(21) Appl. No.: 17/247,457

(22) Filed: Dec. 11, 2020

(51) Int. Cl.
| | |
|---|---|
| *A61L 2/22* | (2006.01) |
| *B66B 1/52* | (2006.01) |
| *A61L 2/24* | (2006.01) |
| *A61L 2/26* | (2006.01) |

(52) U.S. Cl.
CPC ........ *A61L 2/22* (2013.01); *A61L 2/24* (2013.01); *A61L 2/26* (2013.01); *B66B 1/52* (2013.01); *A61L 2202/14* (2013.01); *A61L 2202/15* (2013.01); *A61L 2202/16* (2013.01)

(58) Field of Classification Search
CPC .................................. A61L 2/22; B66B 1/52
See application file for complete search history.

(56) References Cited

U.S. PATENT DOCUMENTS

| | | |
|---|---|---|
| 4,044,860 A | 8/1977 | Kaneko |
| 5,149,986 A | 9/1992 | Jalbert |
| 6,161,655 A | 12/2000 | Lejon |
| 8,872,387 B2 | 10/2014 | Yoon |
| 9,463,955 B2 | 10/2016 | Preston |
| 10,023,427 B2 | 7/2018 | Scoville et al. |
| 10,618,773 B2 | 4/2020 | yoon |

FOREIGN PATENT DOCUMENTS

CN   210824966 U   *   6/2020

OTHER PUBLICATIONS

English Translation of Chinese Document No. CN 210824966 U provided by the European Patent Office Website espacenet.com: Chen Hezhang; Chen Zhuo: High-Efficiency Automatic Sterilization device for Elevator Keys: Jun. 23, 2020 (Year: 2020).*

* cited by examiner

*Primary Examiner* — Kevin Joyner

(57) ABSTRACT

A touchless and motion-sensing hand sanitizing dispenser that functions as an elevator call button. This invention is intended as a hallway call button retrofit device for existing systems, and it will also benefit both new and modernized installations. In addition to improving on public hygiene, this call system improves on the functionality of conventional call systems by obtaining a better estimate of the people waiting for the elevator in a given direction. This invention will also collect utilization and performance data for the elevator system.

16 Claims, 9 Drawing Sheets

Touchless Sanitizing Elevator Button

Touchless Sanitizing Elevator Button

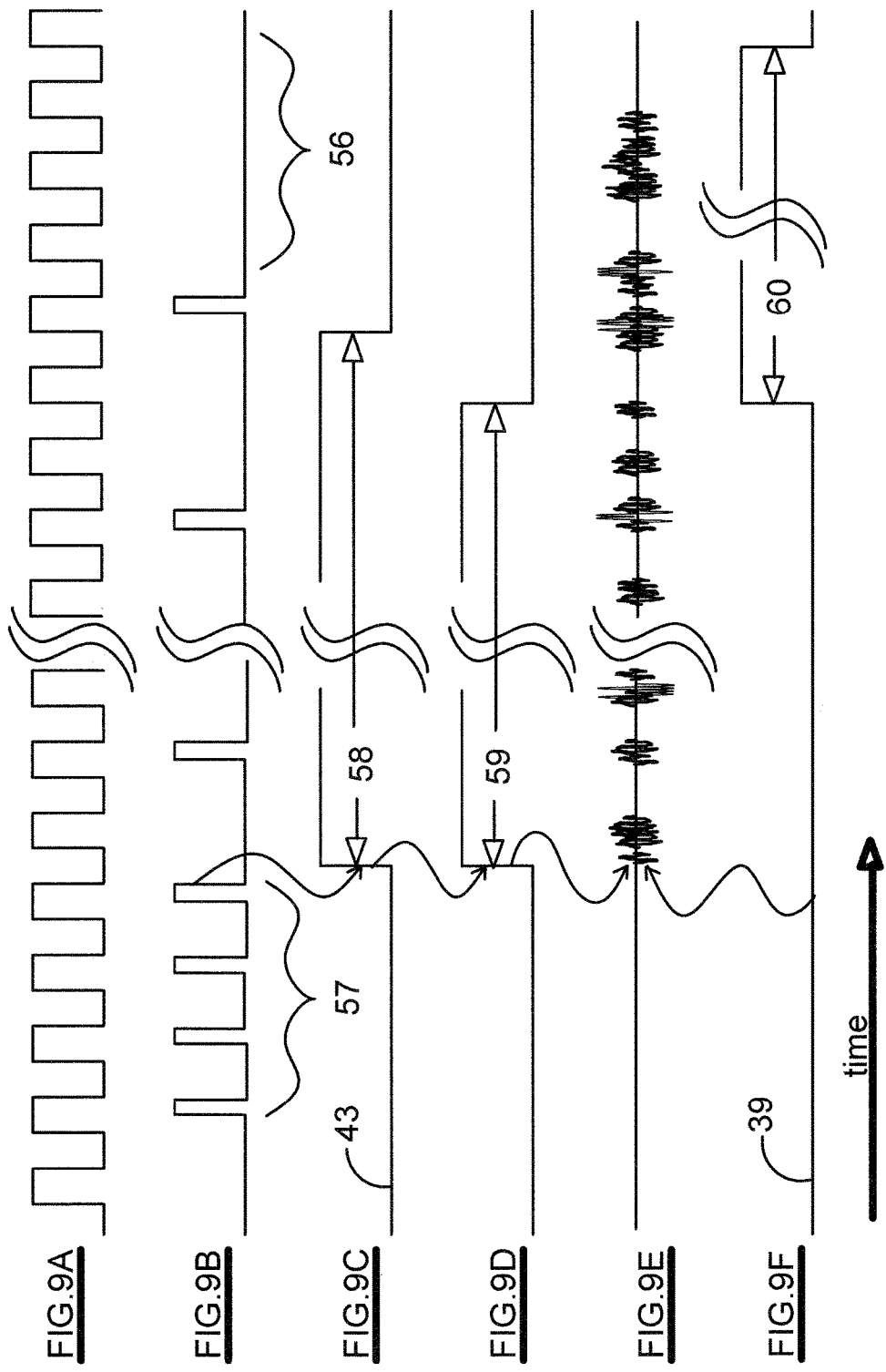

TOUCHLESS SANITIZING ELEVATOR BUTTON

CROSS REFERENCE TO RELATED APPLICATION

Touchless Sanitizing Elevator Button Replacement 62/704,787

STATEMENT OF FEDERALLY SPONSORED RESEARCH

Not Applicable.

THE NAMES OF PARTIES TO A JOINT RESEARCH AGREEMENT

Not Applicable.

REFERENCE TO A SEQUENCE LISTING

Not Applicable.

BACKGROUND OF THE INVENTION

Recent developments in elevator systems referred to as "destination elevators" have heralded the demise of traditional elevator hallway call buttons. These new systems replace hallway call buttons with touch screens, or keypads, and displays. These new elevator call systems have a number of shortcomings but more importantly they do nothing to improve public health and hygiene for the elevator passengers.

After the COVID-19 pandemic, the world will never be the same. Anything that can provide a more germ-free environment will be highly desirable for public use. Even before COVID-19, the design of public spaces has seen a trend toward touchless and motion-sensing equipment, notably in sinks and light switches. The general population is also familiar with the appearance and operation of hand sanitizer dispensers. This invention makes use of the public's increasing familiarity with touchless technology as well as the increasing demand for sanitary conditions in public spaces. Hallway mounted elevator call buttons are germ-ridden surfaces, as are the floor selection buttons in an elevator car. This invention allows people to call for an elevator by making their hands cleaner rather than dirtier.

Some of the related prior art in this area is as follows:

U.S. Pat. No. 6,161,655 Non-contact Elevator Call Button: This invention employs infrared beams with a fixed reflection point in unprotected space 3 inches from the device surface. Some of the drawbacks:
  User training is mentioned and would be required.
  Motion sensing is not mentioned, but even with it there will be a high number of unintended button activations by people and devices passing by.
  No attempt is made to clean the passengers' hands or collect advanced traffic data.

U.S. Pat. No. 10,023,427 B2 Touchless Gesture Recognition For Elevator Service: This invention uses unspecified sensors to sense and recognize hand movements in an open and unrestricted space. Some of the drawbacks:
  User training would be extensive and gesture systems are not known for their reliability.
  Given the open nature of the sensing area, a number of unintended button activations will result from normal activity in that area.
  No attempt is made to clean the passengers' hands or collect advanced traffic data.

U.S. Pat. No. 8,872,387 B2 Non-contact Selection Switch: This invention makes use of interrupted optical beams in a confined space. Some of the drawbacks:
  In an attempt to meet ADA requirements this device is combined with conventional buttons. This is confusing and will require special training to see the main benefit.
  The device opening is narrow and it is intended for operation with one finger. This limited space makes it difficult for most passengers to achieve a non-contact activation.
  No attempt is made to clean the passengers' hands or collect advanced traffic data.

The following two different patents have similar drawbacks:

U.S. Pat. No. 9,463,955 B2 Elevator Operator Interface With Virtual Activation:

U.S. Pat. No. 10,618,773 B2 Elevator Operation Control Device and Method Using Monitor: These two inventions both use vision systems to perform a spatial recognition of a finger that is positioned over a key on a keyboard. These systems will then activate a button on the keyboard when a finger is positioned over the button but not touching it. Some of the drawbacks:
  Both of these inventions are intended for use with destination dispatching systems which are very complex and require extensive user training in addition to the non-contact nature of the keyboard system.
  For this system to work, it will need to have a defined finger dwell time over a button. If this dwell time is too short, it will result in false activations, as fingers move around the keyboard. If the dwell time is too long, it will result in frustration and button contact.
  No attempt is made to clean the passengers' hands or collect advanced traffic data.

U.S. Pat. No. 5,149,986 Electronic Control Button Operated By Sound Absorption: This invention is the first known use of ultrasound in an elevator button. Some of the drawbacks:
  It is a contact style device.
  No attempt is made to clean the passengers' hands or collect advanced traffic data.

U.S. Pat. No. 4,044,860 Elevator Traffic Demand Detector: This invention is an extremely complex collection of sensors and software. The sole purpose of this invention is to collect advanced traffic demand data for the elevator system. The high cost of installing and maintaining such a complex system only serves to emphasize the importance of this data which is critical to improving elevator performance. The disadvantage would be the high cost and complexity of the system.

BRIEF SUMMARY OF THE INVENTION

This invention constitutes a paradigm shift in elevator call systems. It replaces elevator hallway call buttons with a dispenser. The dispenser is a non-contact, motion-sensing, hand sanitizing device that signals a call for the elevator while dispensing hand sanitizing solution or aerosol. Passengers will receive confirmation of their call request by means of a voice acknowledgment of the selected direction request, and the conventional button illumination, controlled remotely by the elevator control system per ADA requirements.

The widespread use of motion-sensor technology and hand sanitizer dispensers would allow this device to be accepted and understood by the public with little or no instruction. It can be retrofitted for button replacement in existing systems or installed in new ones. In new and modernized systems, it would provide valuable data to the elevator's control system. Conventional elevator call buttons illuminate once the elevator control system recognizes the call request. The public is aware that, once a button is illuminated, there is no benefit to additional activations of the button. Thus, the existing call button system provides no quantitative data to the elevator control system as to the number of passengers waiting to travel in a specific direction. With the use of this invention, if there is a group of people waiting for the elevator, most people will also partake and accept a dose of hand sanitizing solution or aerosol. This change in passenger behavior represents the paradigm shift of this invention. Each dose of hand sanitizing solution or aerosol that is dispensed will send an additional button activation signal to the elevator control system. This would allow the elevator control system to improve dispatching and cut down on wait times, because it would provide a count of how many people are waiting for the elevator in a given direction.

By providing a touchless system that simultaneously dispenses hand sanitizing solution or aerosol and registers a call for elevator service, this device will provide a significant competitive advantage by making elevator doors, car interiors, and floor selection buttons cleaner and safer.

It should be noted that if the dispensing system malfunctions or runs empty, the call function will continue to operate.

These and other objects, features, and advantages of the present invention will become more apparent in light of the detailed description of the preferred embodiment thereof, as illustrated in the accompanying drawings.

BRIEF DESCRIPTION OF THE DRAWINGS

FIG. 9 Is a timing diagram of the high-level system functions.

DETAILED DESCRIPTION OF THE INVENTION

Figure 1:
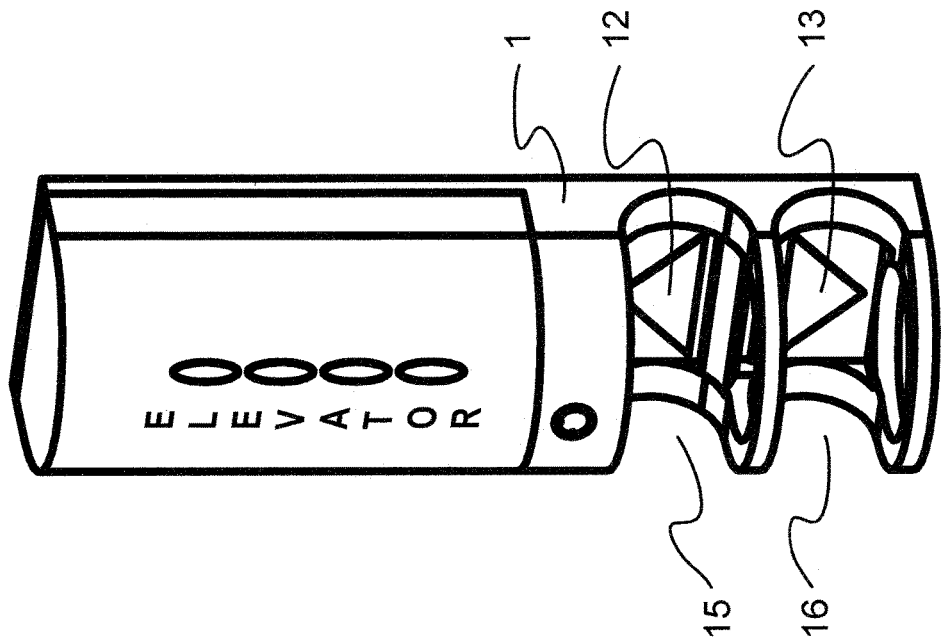
FIG. 1 Is a perspective view of the invention.

FIG. 1 is a perspective view of the Touchless Sanitizing Elevator Button 1, which by design has the appearance of a dispensing device but also has elements of an elevator's hallway up/down call button fixture by virtue of the two open dispensing bays 15, 16, each containing a direction arrow button target 12, 13. The present invention has an UP button dispensing bay 15 with a raised green UP arrow button target 12 at the back wall and a DOWN button dispensing bay 16, with a raised red DOWN arrow button target 13, also at the back wall. It is a standard arrangement for elevator systems to remotely control the illumination of elevator call buttons. This operating method ensures that the elevator system has acknowledged the call request and also allows multiple call buttons on the same floor to operate in unison. Pushing one button will illuminate all buttons that are part of an elevator group. This invention conforms to the industry and ADA standards for illumination of the UP and DOWN arrow button targets 12, 13. It is important to note that the UP and DOWN arrow button targets 12, 13 can be illuminated, but their shape and color are still clearly visible without illumination.

Figure 2:
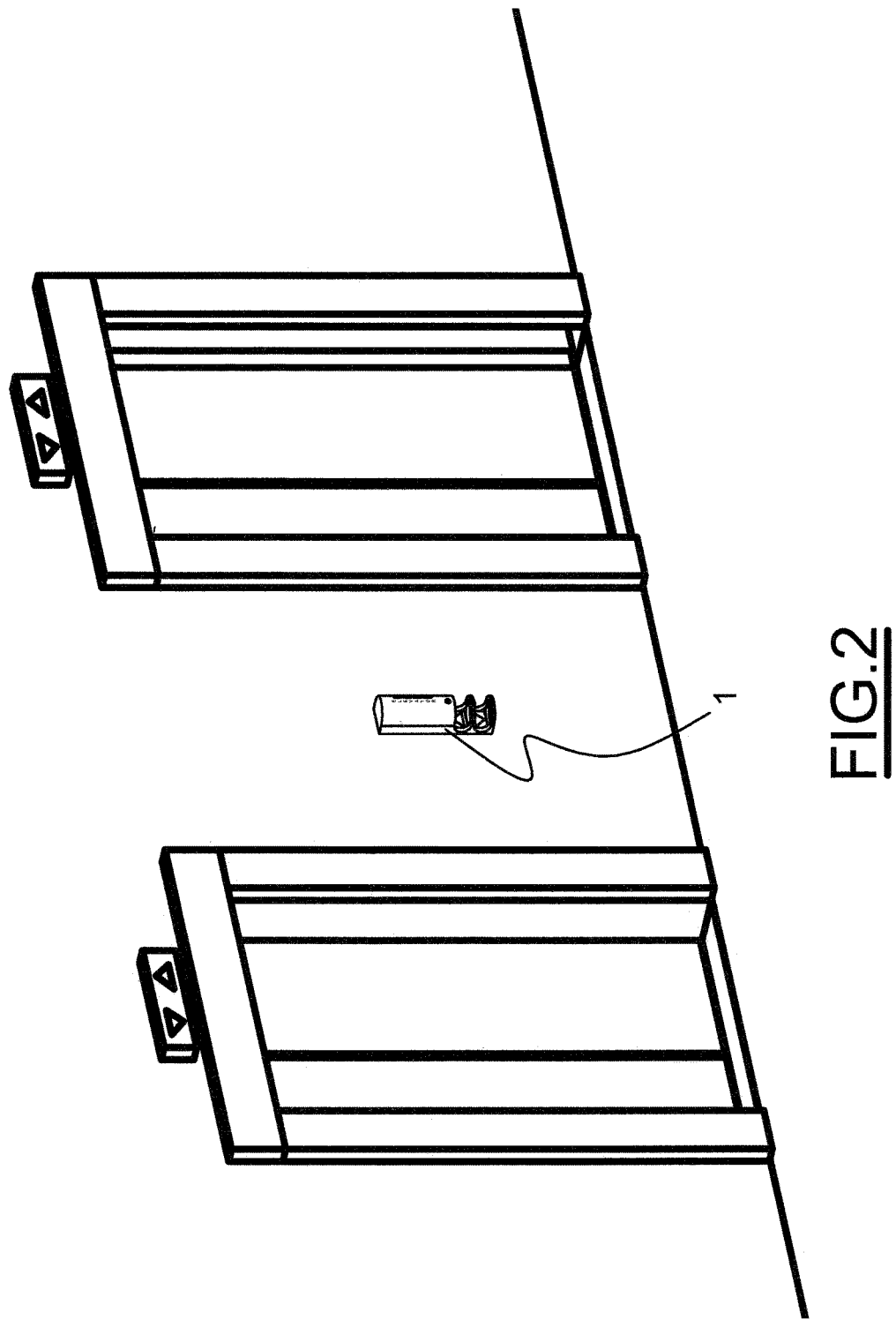
FIG. 2 Is a perspective view of the invention installed in an elevator lobby.

FIG. 2 is a perspective view of the invention as installed in a hallway in place of traditional elevator call buttons.

Figure 3A:
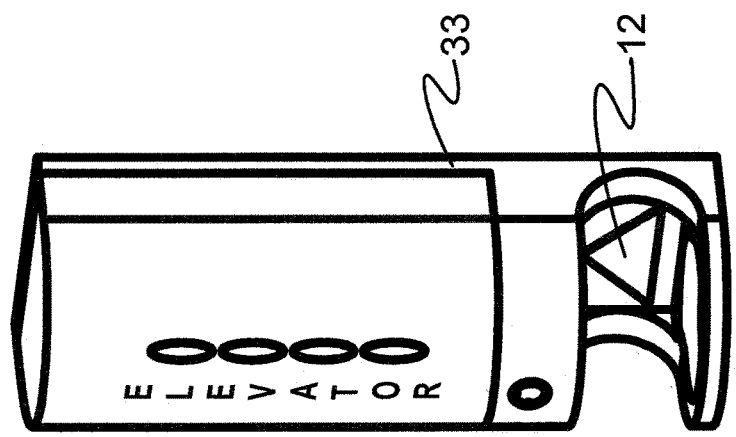
FIG. 3A Is a perspective view of a single station device that would be employed at the bottom floor.
Figure 3B:
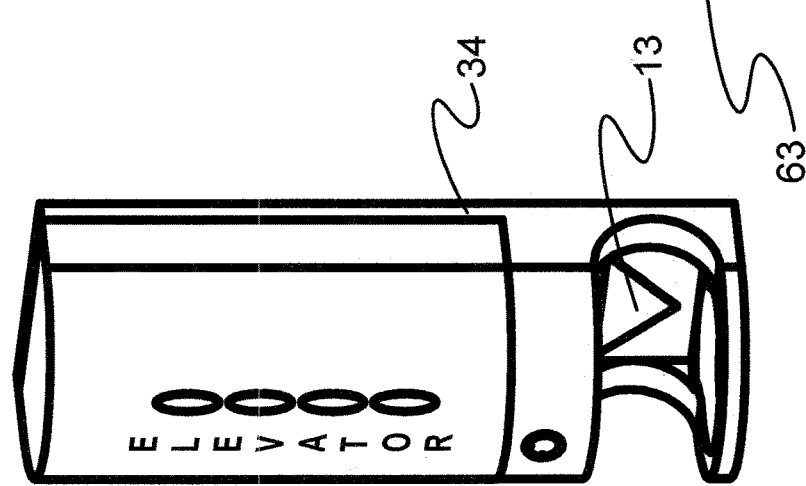
FIG. 3B Is a perspective view of a single station device that would be employed at the top floor.
Figure 3C:
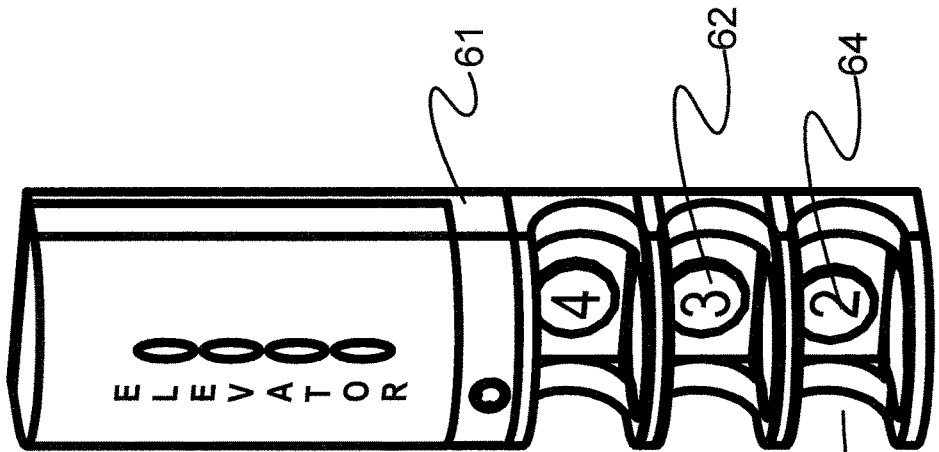
FIG. 3C Is a perspective view of a multi station device that would be employed for direct floor entry.

FIGS. 3A, 3B, and 3C represent variations on the present invention 1 that are necessary to accommodate a full set of system input requirements.

FIG. 3A is the terminal landing UP button version 33 and FIG. 3B is the terminal landing DOWN button version 34. The two single station versions 33, 34 are a subset of the present invention 1 in that they each have only a single button dispensing bay 63 and each has a different direction arrow button target 12, 13.

FIG. 3C is a multi button version 61 which is used for direct floor selection requests. The multi button version 61 is a super-set of the present invention 1. In the multi button version 61 there are a plurality of dispensing bays 63 and the direction arrow button targets 12, 13 are replaced by round and raised floor selection button targets 62. Additionally, the floor selection button targets 62 are labeled with alphanumeric characters 64 to represent the destination floors that are available for selection.

Anyone skilled in the art can use a subset of the present invention 1 to create the single station versions 33 and 34 and a super-set of the present invention 1 to create the multi-button version 61.

Figure 4:
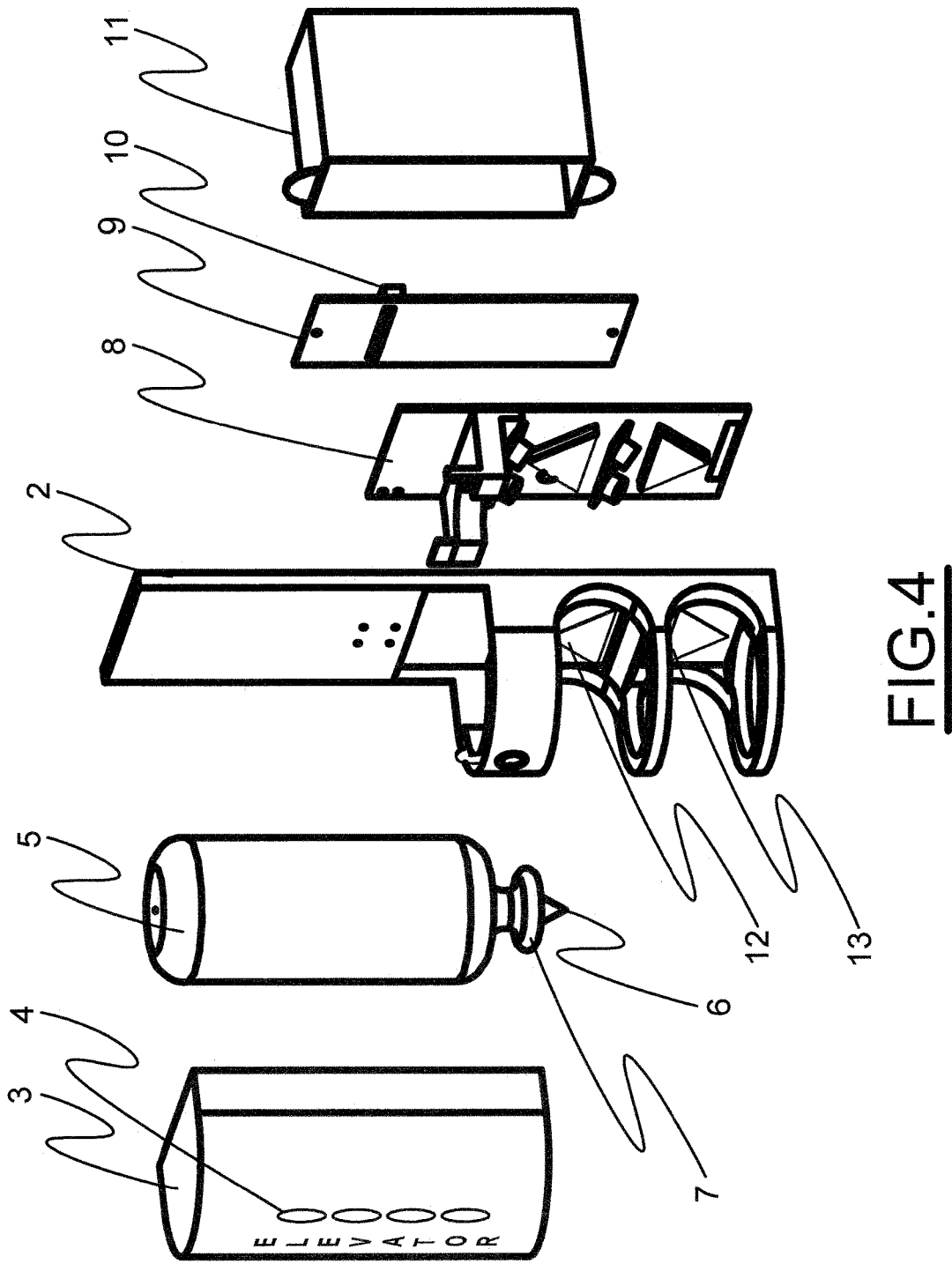
FIG. 4 Is an exploded view of the invention identifying the major components of the up/down device.

FIG. 4 is an exploded view of the invention 1 that illustrates the major components of the invention 1. The button housing 2 is constructed of metal or a durable equivalent and the raised arrow button targets 12 and 13 are constructed with translucent material to allow for illumination from the rear. There is a removable dispenser cover 3 that includes cover windows 4 to view the level of dispensing solution. There is a removable and transparent dispensing reservoir assembly 5 with an integrated release actuator including a connector 31, an electric pump 7, and a dispensing nozzle 6. As is the case with soap dispensers, this dispensing reservoir assembly 5 must be replaced or refilled routinely. The control circuit assembly 8 is shown in its relative position. The wall box 11 used for field wiring is shown for reference and is not part of the invention. There is a box cover and mounting plate 9. The mounting plate 9 includes a wiring terminal block 10 that is provided for connecting field wiring.

Figure 5:
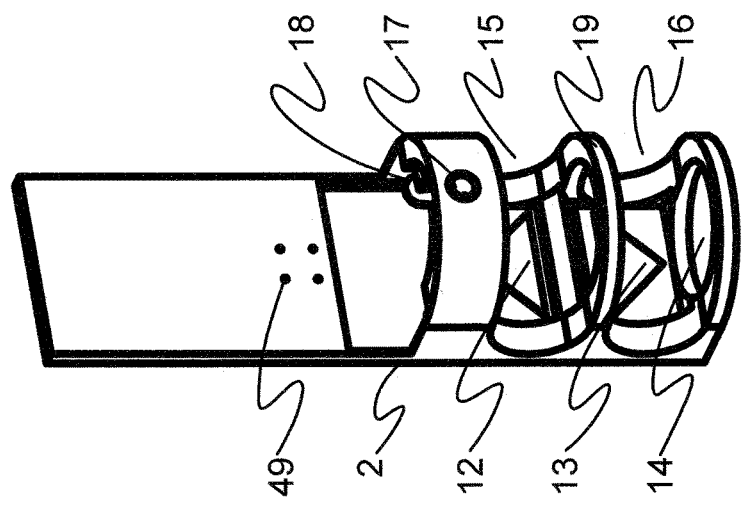
FIG. 5 provides a perspective view of the up/down device housing 2 and its key components.

FIG. 5 is a perspective view of the button housing 2. The button housing 2 includes an UP button dispensing bay 15 and a DOWN button dispensing bay 16. The two button dispensing bays 15, 16 are separated by a separating element 19 that is integrated into the main housing 2. This separating element 19 allows the two button dispensing bays 15, 16 to be serviced by one dispensing reservoir assembly 5.

The present invention 1 makes use of a shared tandem dispensing system for the hand sanitizing solution or aerosol and this is the preferred embodiment when there are multiple dispensing bays 15 and 16. However, separate dispensing systems can also be implemented by one skilled in the art.

The base of the button housing 2 includes a drip pan 14, which is typical for this type of dispenser system. The UP button dispensing bay 15 includes a raised green direction arrow button target 12 on the back wall of the button housing 2 that can be illuminated from behind. The DOWN button dispensing bay 16 includes a raised red direction arrow button target 13 on the back wall of the button housing 2 that can be illuminated from behind. These raised direction arrow button targets 12, 13 will provide a button target for the visually impaired passengers. The preferred minimum height of each dispensing bay 15, 16 is 3 inches. The button housing 2 includes mounting holes 49 that allow for the secure attachment of the button housing 2 to the mounting plate 9 and the wall. The actual mounting fasteners are not shown. The button housing 2 includes a cover lock 17 and a cover latch 18 to secure the dispenser cover 3 in place. The cover lock 17 ensures that only authorized personnel will have access to replace or refill the dispensing reservoir assembly 5.

Figure 6:
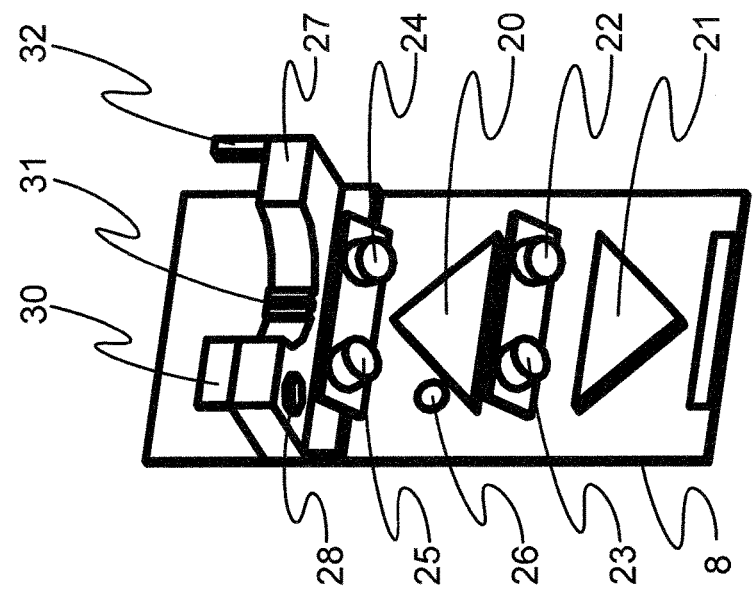
FIG. 6 provides a perspective view of the up/down device control circuit and its key components.

FIG. 6 is a perspective view of the control circuit assembly 8. The control circuit assembly 8 includes an integrated green UP arrow LED array 20 and an integrated red DOWN arrow LED array 21. Each of the two button dispensing bays 15, 16 have an object sensing system. Each of the object sensing systems is comprised of a pair of focused ultrasound devices that are aimed at the center of each dispensing bay 15, 16. The ultrasound transmitter 22 and the corresponding ultrasound receiver 23 for the DOWN button dispensing bay 16 are mounted on and integrated with the control circuit assembly 8. Similarly, the ultrasound transmitter 24 and the corresponding ultrasound receiver 25 for the UP button dispensing bay 15 are mounted on, and integrated with, the control circuit assembly 8. Each of the ultrasound transmitters 22 and 24 are focused, high frequency devices and their corresponding ultrasound receivers are also focused, high frequency devices. Each of these transmitter and receiver pairs 24 and 25 and 22 and 23 are aimed at the center of their respective button dispensing bays 15 and 16. By aiming the transmitter and receiver pairs 22 and 23 and 24 and 25 at these centers, they will be able to echo-locate any physical item in the center of the button dispensing bays 15 and 16, including hands and any other type of objects. A software-based motion detection algorithm is employed to preclude any measurement errors that may result from speed of sound variations due to temperature and humidity changes.

It should be noted that a number of sensing technologies can be implemented to detect object motion in the dispensing bays 15 and 16. Here are some examples of the less preferred technologies:

a) It is possible to use one sensing system for all of the dispensing bays.

b) It is also possible to use a single ultrasound transducer that functions both as a transmitter and as a receiver. This is a common practice for echo-location systems. However, in this case the distances are short and this can cause signal problems.

c) Much of the prior art makes use of optical or infrared beams both in reflected and interrupted modes. These technologies can work as well but they can also provide a safety hazard if they are sensitive to fire or smoke conditions. Modern elevator systems use a system of integrated smoke alarms to protect its passengers in the event of a fire but these systems are not redundant and smoke alarms can fail or can be slow to respond. In the event of a problem with the smoke detectors, elevator passengers can be put at risk if the elevator hallway call buttons are sensitive to smoke or fire conditions.

The control circuit assembly 8 includes a high temperature limit 26 that serves to prevent malfunctions of the device by disconnecting the device power in the event of a nearby high temperature condition.

A control circuit assembly frame 27 and a dispensing reservoir assembly connector 31 interface with and connect to the dispensing reservoir assembly 5.

An audio speaker 28 is also mounted on the control circuit assembly frame 27. The purpose of the audio speaker 28 is to enable an audio confirmation phrase of the selected elevator request such as "up request" or "down request" to confirm the user request. Given that this invention is different from traditional elevator buttons, the additional feedback provided by an audio message will reassure passengers that no further action on their part is required. This optional audio confirmation phrase can be turned off or limited to the first request for service in a given direction. This audio phrase is not a replacement for the confirmation of the elevator system in the form of the direction arrow illumination signals 39, 40.

The present invention 1 will also include an optional non-dispensing mode of operation to accommodate passengers that are averse to or allergic to the sanitizing solution or aerosol. This mode will recognize a rapid swipe through the dispensing bay 15 or 16 and process the elevator call request but the sanitizing solution or aerosol will not be dispensed.

The control circuit assembly 8 includes a setup and diagnostic mode to allow for initial setup, system adjustments, and data access. Anyone skilled in the art could provide an alternate and suitable interface to achieve these functions. The following description defines the preferred embodiment.

The control circuit assembly frame 27 also includes an optical cover sensor and a Near Field Communication (NFC) antenna 30. When the dispenser cover 3 is removed, the optical cover sensor 32 will force the system into diagnostic and setup mode. An app on a smartphone will communicate with the microcontroller 35 via an NFC antenna 30 and an NFC Interface 36. The smartphone app will allow for parameter adjustments and for the downloading of performance data. Some of the key adjustment parameters are: motion sensitivity, dispensing time, audio response ON/OFF, language, phrase selection, and signal configurations.

Figure 7:
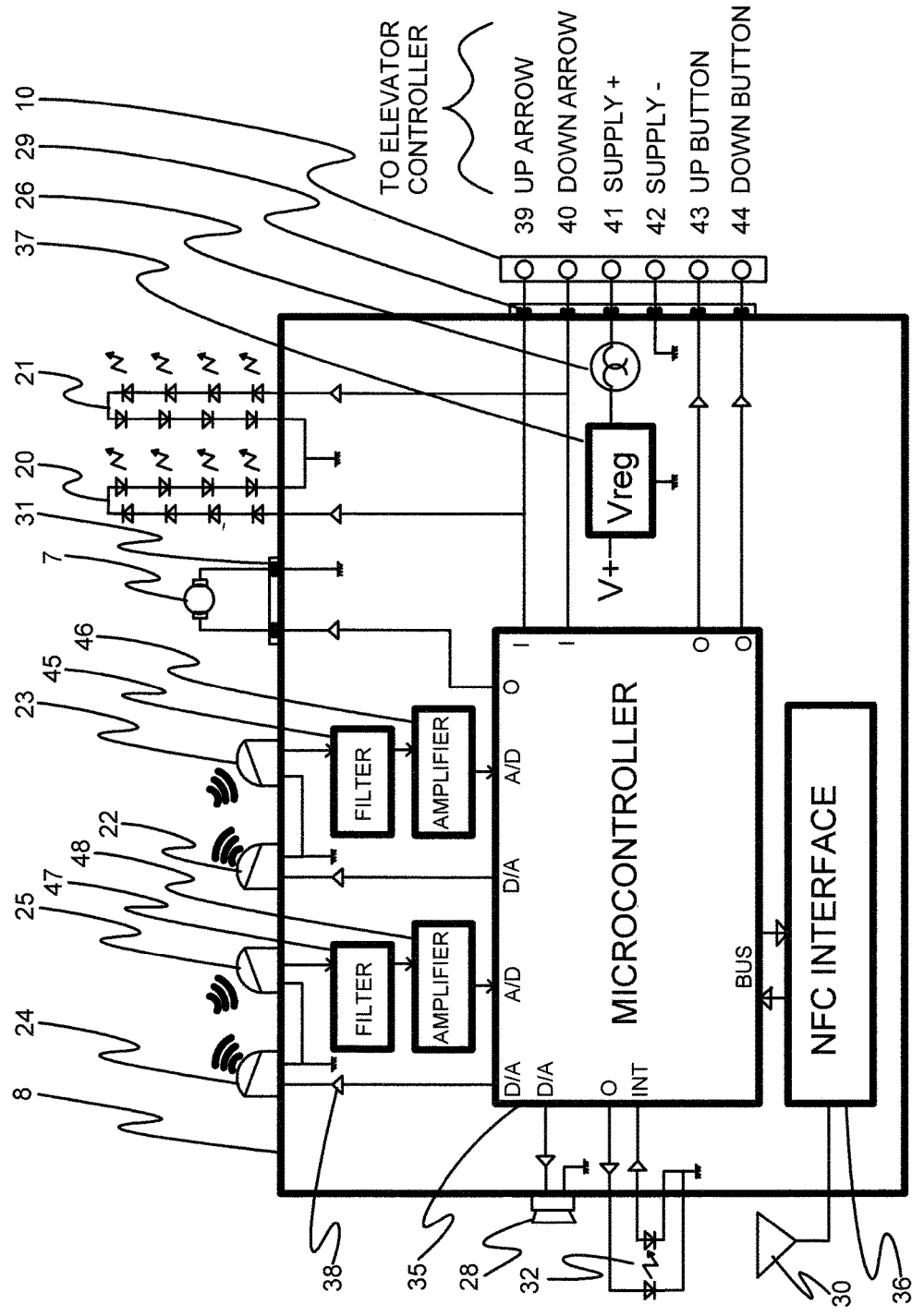
FIG. 7 Is a functional block diagram of the up/down device electronics.

FIG. 7 provides a logical view of the control circuit assembly 8 in the form of a block diagram. FIG. 7 includes all of the items described in FIG. 6 and some additional items necessary to complete the invention. The control circuit assembly 8 includes a microcontroller 35 which will perform all the logic and data processing functions necessary for the device functions. A Near Field Communication (NFC) Interface 36 will manage all the device's wireless communication in the maintenance and diagnostic mode of operation between the microcontroller 35 and a smartphone app. A voltage regulator circuit 37 is included to maintain a stable operating voltage for the components on the control circuit assembly 8. A number of microcontroller buffer interface circuits 38 are required to interface the board mounted components. The DOWN ultrasound receiver 23 interfaces with a high pass filter circuit 45 and an amplifier circuit 46 prior to interfacing with an analog to digital converter on the microcontroller. The UP ultrasound receiver 25 interfaces with a high pass filter circuit 47 and an amplifier circuit 48 prior to interfacing with an analog to digital converter on the microcontroller.

The microcontroller 35 includes a real time clock as part of its operating software. The real time clock is not necessary for button operation but is provided to allow the microcontroller 35 to collect and store both usage and performance data for the system. The collected data can be downloaded into a smartphone app via the NFC Interface in the maintenance and diagnostic mode.

The six-wire interface between the present invention 1 and the elevator control system represents the simplest form of the elevator interface. These connections are made at the field wiring terminal block 10. The field wiring terminal block 10 is connected to the control circuit assembly 8 by a connector 29 that is located on the back side of the control circuit assembly 8. The elevator system provides power in the form of a positive DC supply voltage 41 and a supply voltage return 42. The elevator system also provides an UP arrow illumination signal 39 and a DOWN arrow illumination signal 40. These two signals 39, 40 are completely controlled by the elevator control system, but they are monitored by the microcontroller 35 for the purposes of performance monitoring and audio announcement function. The UP arrow illumination signal 39 will cause the UP arrow LED array 20 to illuminate. The DOWN arrow illumination signal 40 will cause the DOWN arrow LED array 21 to illuminate. The illumination of either of these LED arrays 20, 21 is an acknowledgement by the elevator control system that the call for service request has been acknowledged and an elevator is en route. The duration of the UP and DOWN arrow illumination signals 39, 40 are a measure of elevator response time. The UP button signal 43 is a button activation signal generated by the microcontroller 35. The DOWN button signal 44 is a button activation signal generated by the microcontroller 35. Both of these button signals 43, 44 have programmable active levels and durations to accommodate retrofit situations.

Figure 8:
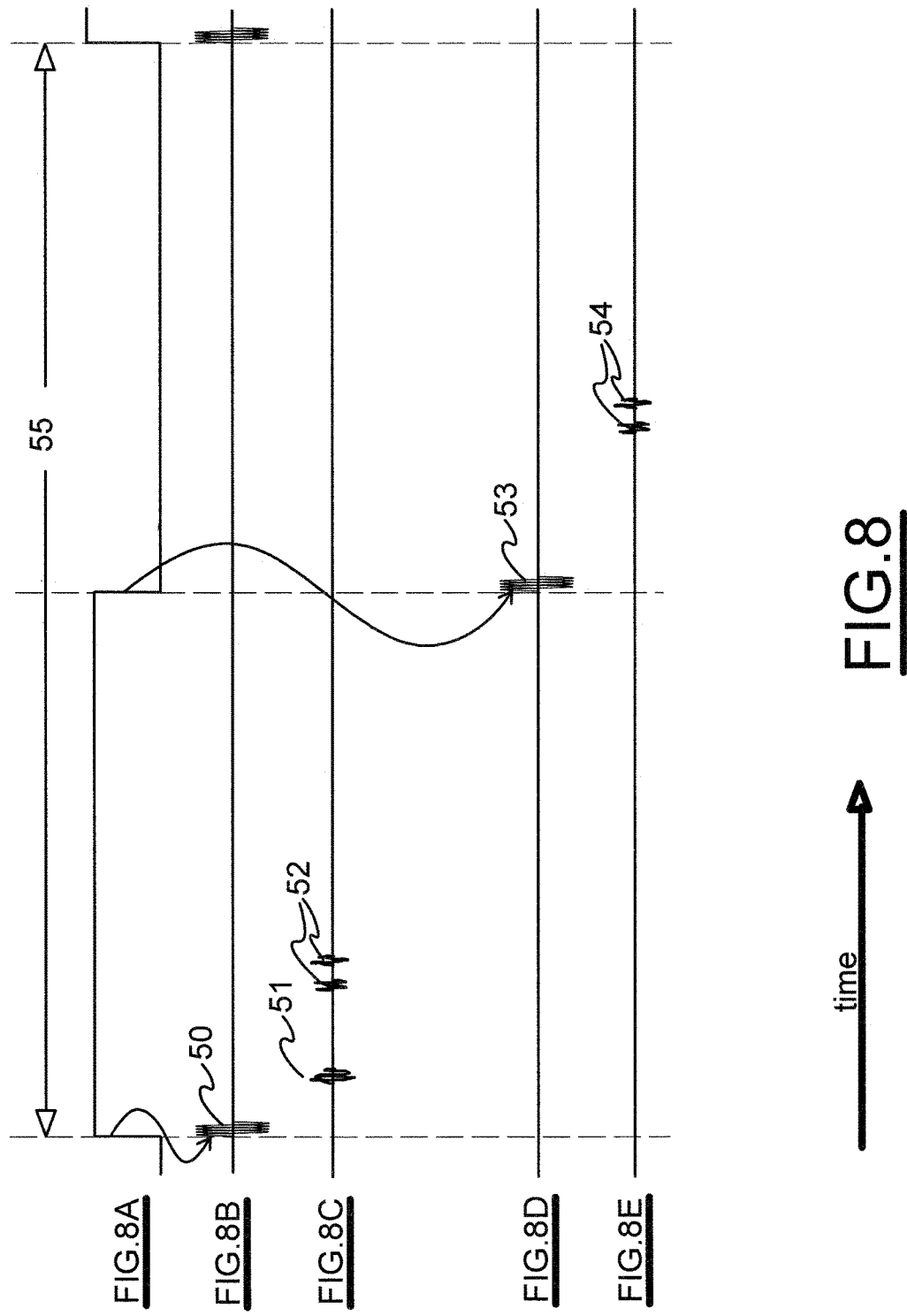
FIG. 8 Is a timing diagram of the echo-location detecting system.

FIG. 8 is a timing diagram that provides additional details on how the ultrasonic transmitters 22, 24 and the receivers 23, 25 are controlled by the microcontroller 35 to detect motion in the button dispensing bays 15, 16. Each of the ultrasonic transmitters 22, 24 is operated in a burst mode and the bursts are repeated at a 20 hertz rate. FIG. 8A is a representation of the microcontroller cycle rate and it has a period 55 equal to 50 milliseconds. The cycle rate shown in FIG. 8A is an internal signal for the microcontroller 35 and period 55 is split into two equal halves of 25 milliseconds each. The first half of the cycle is used for the UP button dispensing bay 15 measurement and the second half is used for the DOWN button dispensing bay 16 measurement. At the beginning of the cycle, the microcontroller 35 will generate a transmission burst 50 shown in FIG. 8B of four cycles at a 50 KHZ rate for the UP ultrasound transmitter 24. FIG. 8C is the waveform that is received by the microcontroller 35 after the received ultrasound echoes from the ultrasound receiver 25 have been filtered and amplified. The received signal in FIG. 8C includes an ultrasound echo from an active target signal 51 from an object located in or near the center of the UP button dispensing bay 15 as well as multiple echoes from the structure 52 itself. At the second half of the cycle the microcontroller 35 will generate a transmission burst 53 shown in FIG. 8D of four cycles at a 50 KHZ rate for the DOWN ultrasound transmitter 22. The received signal in FIG. 8E includes only multiple echoes 54 from the structure itself, with no objects present in the DOWN button dispensing bay 16. Given that the speed of sound in air varies with both temperature and humidity, the microcontroller 35 will employ motion detection algorithms rather than attempting position-based measurements.

FIG. 9 is a timing diagram that provides details on the high level functioning of the present invention. FIG. 9 illustrates the signals for the UP button dispensing bay 15, but does not show the signals for the DOWN button dispensing bay 16, which would be similar. FIG. 9A is a higher level view of the internal cycle signal shown in FIG. 8A, wherein each cycle represents an echo sounding in each of the dispensing bays 15, 16. FIG. 9B is a representation of a function internal to the microcontroller 35 and illustrates when motion is or is not detected per echo cycle wherein the high state of FIG. 9B represents that motion has been detected for that cycle. Before any button activation can occur, there is an idle period requirement 56 of at least 20 cycles, or about 1 second, without any motion detected. The activation of an elevator call request is based on a running average of motion detections per cycle exceeding a motion threshold 57. The motion threshold 57 is a setting within the microcontroller that can be used to adjust the sensitivity of the UP and DOWN button dispensing bays 15, 16. FIG. 9C is the UP arrow signal 43 that is sent to the elevator control system in lieu of a mechanical button push. The UP button signal 43 is generated by the microcontroller 35 only after the prerequisite idle period requirement 56 and the motion threshold 57 requirements have been satisfied. The pulse duration of the UP button signal 58 is controlled by the microcontroller and is adjustable to accommodate different elevator system requirements. FIG. 9D represents the dispensing reservoir electric pump activation signal. The hand sanitizing solution dispensing cycle is triggered by the start of the UP button signal 43. Its duration 59 is also an adjustable parameter within the microcontroller 35. FIG. 9E is the optional audio announcement signal sent to the speaker 28 and it is triggered by the start of the dispensing signal shown in FIG. 9D. The audio announcement can be enabled or disabled by a setting within the microcontroller 35. One setting for the audio announcement is to play only on the first call request from that floor and the microcontroller 35 will monitor the UP arrow illumination signal 39 to establish this condition. FIG. 9F represents the UP arrow illumination signal 39 that is provided by the elevator control system. The microcontroller 35 monitors the UP and DOWN arrow illumination signals 39 and 40 for the purposes of data monitoring and reporting. The UP arrow illumination signal duration 60 is a good measure of system response time.

The present invention 1 is implemented with a discrete signal interface between the invention 1 and the elevator control system and this is still a common type of signal communication method for many elevator systems. The control circuit assembly 8 can accommodate a wide range of voltages and logic levels for discrete signals. However, many new and existing systems employ a wide range of serial bus networks for communications between hallway call registering devices and the elevator control system. Anyone skilled in the art can implement a network interface to accommodate the required signal interchange between the present invention 1 and the elevator control system.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A dispenser for dispensing hand sanitizing solution or aerosol, and to function as an elevator call button, the dispenser comprising:
   a) a housing;
   b) a reservoir for holding the hand sanitizing solution or aerosol;
   c) a release actuator for discharging hand sanitizing solution or aerosol from the reservoir;
   d) a number of dispensing bays, including at least one;
   e) an elevator control system;
   f) an elevator interface for each of the dispensing bays;
   g) a number of object sensing systems including at least one, to detect object motion in each of the dispensing bays; and
   h) a control circuit;
   wherein, the control circuit operates the object sensing systems to identify object motion within the dispensing bays;
   wherein the control circuit is configured to activate the release actuator to discharge the hand sanitizing solution or aerosol into the requestor's hand;
   wherein the control circuit will communicate with the elevator control system via the elevator interface to send and acknowledge an elevator service request.

2. The reservoir of claim 1, wherein the reservoir is a refillable component.

3. The release actuator of claim 1, wherein the release actuator is an electric pump for the purpose of discharging a dose of hand sanitizing solution or aerosol into the requestor's hand in the dispensing bay.

4. The release actuator and the reservoir of claim 1, wherein the release actuator and the reservoir can be shared for each of the dispensing bays when there are more than one of the dispensing bays.

5. The elevator interface of claim 1, wherein the elevator interface includes two-way communication with the elevator control system, and is implemented with discrete signals including elevator request signals and elevator feedback signals.

6. The elevator interface of claim 1, wherein the elevator interface includes two-way communication with the elevator control system, and is implemented with a serial bus communication network and includes elevator request signals and elevator feedback signals.

7. The dispensing bays of claim 1, further comprising; a button target located on the rear face of each of the dispensing bays.

8. The button target of claim 7, further comprising the shape and appearance of a control button associated with the elevator control system.

9. The button target of claim 7, further comprising a visual display surface, wherein the visual display surface is controlled by feedback from the elevator control system via the elevator interface.

10. The object sensing system of claim 1, further comprising; an ultrasound transmitter and an ultrasound receiver, wherein the ultrasound transmitter and the ultrasound receiver, working as a pair and operated by the control circuit are capable of detecting the motion of a human hand or similar sized object as well as objects as small in shape and size as a human finger.

11. The dispenser of claim 1, further comprising; a number of separator elements to set boundaries between each of the dispensing bays when there are two or more dispensing bays.

12. The dispenser of claim 1, further comprising; an audio announcement function that is controlled by the control circuit, wherein the control circuit can play audio announcements based on motion detection in the dispensing bays and on feedback from the elevator control system.

13. The control circuit of claim 1, wherein the control circuit is a microcontroller.

14. A method for maintaining clean and sanitary surfaces in an enclosed space of an elevator cab by encouraging passengers to accept a free dose of hand sanitizing solution in return for access to the enclosed space, the method comprising dispensing the free dose of hand sanitizing solution from the dispenser of claim 1.

15. A method for collecting advanced elevator traffic flow data for passengers where passengers are rewarded with a free dose of hand sanitizing solution or aerosol in return for registering their travel intentions in advance of entering the elevator, the method comprising dispensing the free dose of hand sanitizing solution or aerosol from the dispenser of claim 1.

16. The method of claim 15, wherein performance and utilization data is collected for the elevator system by recording the time and date for each of these occurrences:
   a) activation of an elevator call request; and
   b) a change in state of any of the arrow illumination signals;
   wherein, the recorded data is maintained for an extended time and is made available for transfer to other devices.

* * * * *